United States Patent [19]

Sato

[11] Patent Number: 4,747,686

[45] Date of Patent: May 31, 1988

[54] METHOD AND APPARATUS FOR PERFORMING NOVEL HIGH-PERFORMANCE LIQUID CHROMATOGRAPHY

[75] Inventor: Haruo Sato, Chiba, Japan

[73] Assignee: SATO Pharmaceutical Research Institute Ltd., Tokyo, Japan

[21] Appl. No.: 889,194

[22] Filed: Jul. 25, 1986

[30] Foreign Application Priority Data

Aug. 9, 1985 [JP] Japan ................. 60-175288

[51] Int. Cl.$^4$ .................. G01N 21/85; G01N 30/74
[52] U.S. Cl. .................. 356/72; 73/61.1 C; 356/410
[58] Field of Search .................. 356/410, 440, 39, 72; 73/61.1 C

[56] References Cited

U.S. PATENT DOCUMENTS

| | | | |
|---|---|---|---|
| 3,492,396 | 1/1970 | Dalton et al. | 356/39 X |
| 4,182,161 | 1/1980 | Greenfield | 356/39 X |
| 4,375,163 | 3/1983 | YANG | 73/61.1 C |
| 4,558,947 | 12/1985 | WARDLAW | 356/39 |
| 4,576,477 | 3/1986 | CORBET ET AL. | 356/39 |
| 4,618,769 | 10/1986 | JOHNSON ET AL. | 356/440 X |

Primary Examiner—Vincent P. McGraw
Attorney, Agent, or Firm—Oblon, Fisher, Spivak, McClelland & Maier

[57] ABSTRACT

This invention relates to an apparatus and a method of high performance liquid chromatography comprising irradiating a high performance liquid chromatography column and detecting separation conditions and separation patterns of a material charged onto said column by measuring the intensity of transmitted light, reflected light or fluorescent light from the column by means of a line sensor.

10 Claims, 9 Drawing Sheets

METHOD AND APPARATUS FOR PERFORMING NOVEL HIGH-PERFORMANCE LIQUID CHROMATOGRAPHY

BACKGROUND OF THE INVENTION

1. Field of the Invention

This invention relates to a method and apparatus for performing novel high-performance liquid chromatography, and more particularly to high-performance liquid chromatography capable of detecting separation patterns in a column.

2. Discussion of the Background

Chromatography is generally classified into gas chromatography and liquid chromatography by the differences in the mobile phase. Liquid chromatography is further categorized into column chromatography (HPLC) and thin layer chromatography (TLC). Recently, high performance thin layer chromatography (HPTLC), which is the same as TLC in principle, has been introduced into the art.

In applications of chromatography as a means of separation, TLC is used mainly for qualitative analysis because of its ease of use, while HPLC is used mainly for quantitative analysis.

The greatest difference between TLC and HPLC is the fact that TLC is an open chromatography system while HPLC is a closed system. In an open system, difficulty is encountered in accurately detecting the sizes and gradation of separated spots due to diffusion of solvents and separated substances. On the other hand, a closed HPLC system, which uses a column of a predetermined volume for separation, is free of the problems mentioned above for TLC so that it is superior in quantitative reproducibility.

Another difference between HPLC and TLC is found in the method of detection after separation. Detection in the open TLC system is via a static method. The spots of the respective components are irradiated with light of a predetermined wavelength after development and separation, either measuring the degree of absorbance of reflected or transmitted light or measuring the fluorescent light intensity after coupling with a fluorescent substance. On the other hand in HPLC, which can be regarded as a dynamic method, the effluent solutes which have been separated in a column according to the retention time of the respective components are detected by measuring the degree of absorbance, fluorescent light intensity or refractive index by means of a detector which is located at the outlet of the column.

Important characteristics in chromatographic analysis are the ability to separate the respective components and the accuracy of the quantitative and qualitative analyses of the separated components. Considering TLC and HPLC from this viewpoint, TLC is disadvantageous since charging of test material in excess of a certain amount is difficult as compared with HPLC and the quantitative analysis is inevitably impaired by the differences in diffusion between the spots of the respective components. On the other hand, TLC has the advantage of an open system in that the entire amount of the charged material can be detected after separation. Namely TLC, in which the charged material is entirely separated and developed on a thin layer sheet, can serve as an excellent means of analysis if accurate quantitative analysis of the respective separated components is available by other means.

On the other hand, in the closed HPLC system, the differences in diffusion experienced in TLC, which depend on the nature of the respective components, seldom occur. Namely, a quantitative analysis of extremely high reproducibility is possible by passing a solution of the components, separately desorbed in the column, through a flow cell of predetermined volume and measuring the light absorbance or fluorescent light intensity of the substances in the flow cell. However, a large problem exists in that sometimes the components of a charged material are not entirely desorbed for separation. Especially in an in-phase HPLC system employing a column packed with silica gel, the residue which remains adsorbed in the column without desorbing cannot be ignored. In order to reduce to a minimum the adsorbed residue in the column, it is the general practice in current HPLC to employ a system which first desorbs out polar substances which would tend to remain adsorbed in the in-phase column, namely, to employ a reverse phase packing material. However, even where a reverse phase column is used, the existence of a residue of a non-polar substance is still probable, making it difficult to desorb out and recover the entire amount of the charge. That is to say, it is difficult to make adequate qualitative and quantitative analyses by conventional HPLC employing the system of detecting and identifying only the substances which are separated and desorbed out of a column. The detection of the adsorbed residual components in a column is impossible regardless of the kind of the packing material. Accordingly, in an analysis of HPLC, one should always consider that a certain percentage of the charged substance remains in the column without being detected. In other words, it is possible with conventional HPLC to make a false determination of subject material present due to failure to detect all of the components of the charged material.

There exists a need, therefore, for a method of high-performance liquid chromatography which does not depend on the detection of eluted subject materials.

SUMMARY OF THE INVENTION

Accordingly, an object of this invention is to provide a method and apparatus for performing high performance liquid chromatography which are not dependent on detecting eluted compounds.

The above object and other objects of the invention which will become apparent from the following specification have been achieved by the present method of high performance liquid chromatography in which the separation patterns in an HPLC column are directly detected instead of detecting the solutes in the effluent from the column as in conventional HPLC analysis.

More particularly, in accordance with the present invention, there is provided a method of chromatography which is characterized by irradiating an HPLC column and detecting the separating conditions of a subject material and separation patterns in the column by measuring the intensity of transmitted light, reflected light or fluorescent light from the column by means of a line sensor.

The apparatus comprises a high performance liquid chromatograph comprising an apparatus for detecting separating conditions and separation patterns in a transparent separation column. The column is located within a light-shielding chamber and substantially the entire length of the column is irradiated with a light source.

Separating conditions and separation patterns are detected by a line sensor.

DETAILED DESCRIPTION OF THE PREFERRED EMBODIMENTS

In FIGS. 3-20, the letters A-D designate the following compounds:
A: Protoporphyrindimethylester
B: 3-hydroxyethyl-8-vinyldeuteroporphyrindimethylester
C: 3-vinyl-8-hydroxyethyldeuteroporphyrindimethylester
D: Hematoporphyrindimethylester The fundamental difference in the high-performance liquid chromatography method of the present invention from its conventional counterpart resides in the fact that the column itself (which includes all of the column constituents such as packing material, tubes, desorbing solvent, subject materal etc. unless otherwise specified) is regarded as the subject for detection. Accordingly, in order to permit measurement of the intensity of reflected light, transmitted light or fluorescent light resulting from irradiation of a column, it is normally required to employ a column which is a tube of glass and, especially in a case of measuring absorbed or emitted light in an ultraviolet region, to employ a quartz column. Further, it is necessary to prevent decomposition or reaction by irradiation of the charged sample material or separated components. One reliable method for preventing such decomposition or reaction is to employ a brief irradiation, namely irradiation by light pulses of a short period, while measuring the intensity of transmitted, reflected or fluorescent light due to the brief irradiation. More specifically, this can be accomplished, for example, by synchronizing a line sensor with a pulsed xenon light source and its pulses. In cases where there is no possibility of decomposition or reaction, the irradiation of a column can be carried out in the ordinary manner, while measuring the light intensity by a line sensor. It is desirable to locate the line sensor parallel with the length of the column in such a manner as to cover the light intensity even in the vicinity of the inlet of the column. This is because the line sensor should detect not only the separation patterns in the column but also the separating conditions as a whole, including residual components adsorbed in the vicinity of the inlet of the column.

As will be understood from the foregoing description, the method of high-performance liquid chromatography according to the present invention is similar to the conventional methods in operational procedures except for the method of detecting the separated components and the use of a glass column. If desired, it may be used in combination with a conventional method.

Reference is now made to the drawings which illustrate by way of example an apparatus suitable for carrying out the method of the present invention.

Figure 1:
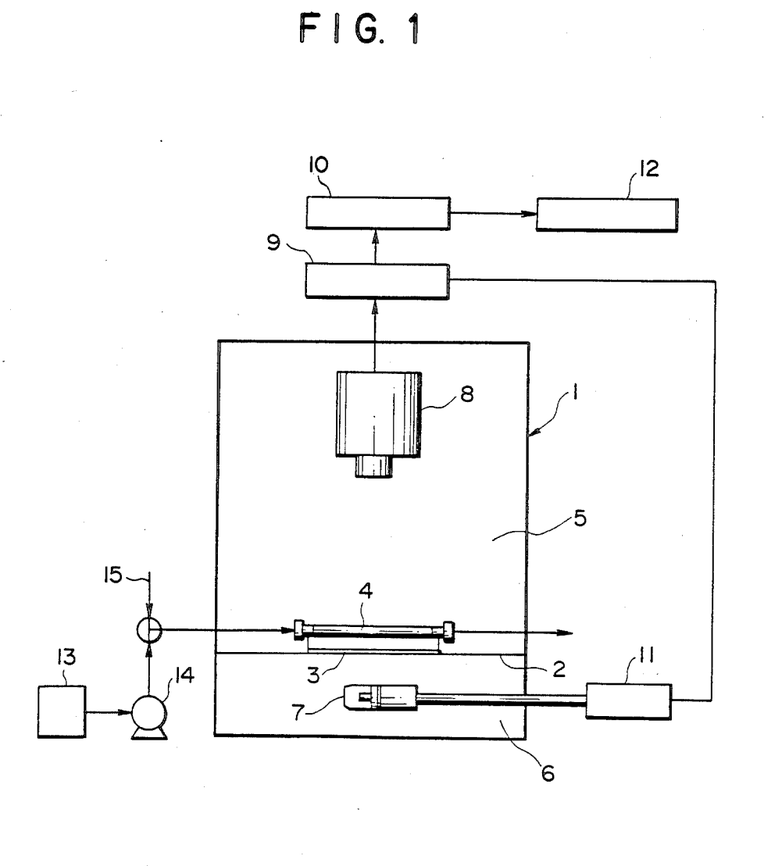
FIGS. 1 and 2 are diagrammatic plan views of an apparatus suitable for carrying out the method of high-performance liquid chromatography according to the invention.

Referring first to FIG. 1, an exemplary embodiment is shown of the apparatus for irradiating pulsed light as mentioned hereinbefore, in which a light shielding box 1 is internally divided into two chambers by a partition wall 2 with a slit 3. A column 4 is located in chamber 5 of the light shielding box 1 parallel to the slit 3. Reference numeral 7 denotes a light source in the form of a pulse lamp which is mounted in the other chamber 6. The pulse lamp 7 faces the column 4 through the slit 3. A line sensor 8 is mounted in chamber 5 in such a manner as to face the pulse lamp 7 through column 4. Designated at 9 is an A/D converter which is connected to the line sensor 8 at a position outside the light shielding box 1 for accepting a sensed light signal from the sensor 8. A computer 10 is connected to the A/D converter 9 to automatically control the synchronized operations of the line sensor 8 and pulsing circuitry 11 of the pulse lamp 7. A floppy disk 12 is connected to the computer 10 to record the data.

Indicated at 13 is a desorbing solvent, at 14 a quantitative pump, and at 15 a sample injector.

With the above-described apparatus, the transmitted pulse of light irradiation is detected by the line sensor 8 before charging of a sample material and at certain time intervals after charging of a sample material, and its output signal is sent through the A/D converter 9 to the computer for processing and the resulting data is stored on the floppy disk 12 at predetermined time intervals. Thus, the separation patterns can be observed at any time by taking out and processing the data which are stored on the floppy disk 12.

Figure 2:
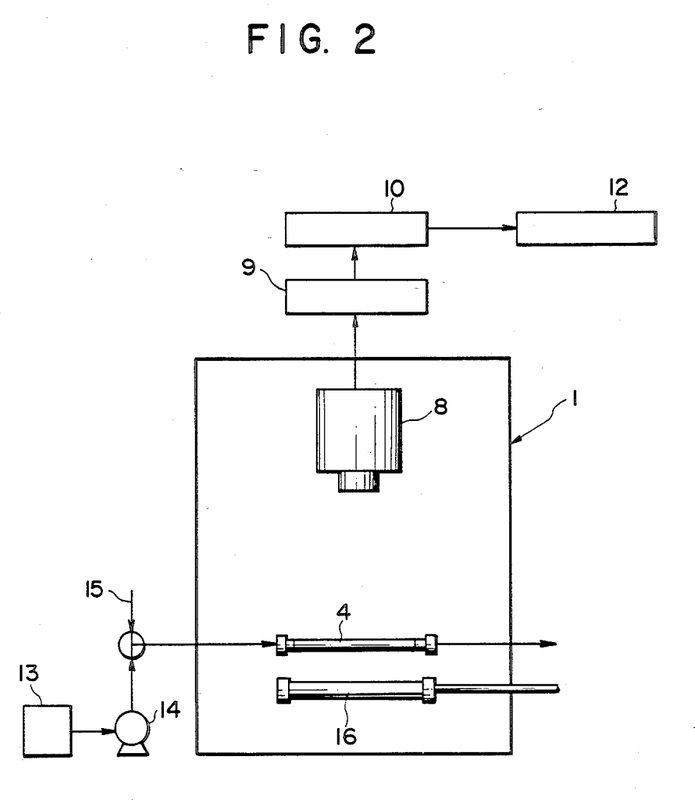
Figure 3:
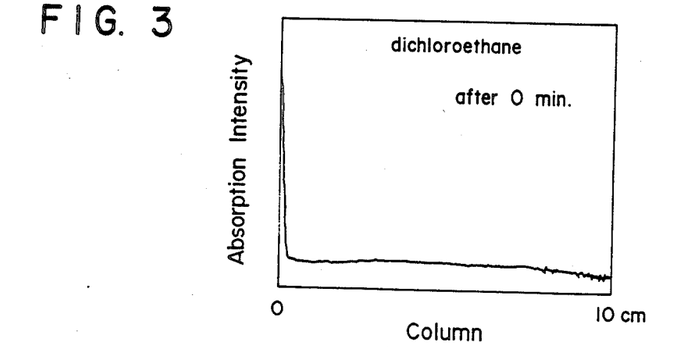
FIGS. 3 to 17 are diagrams of separation patterns obtained at predetermined time intervals after initiation of desorption in Example 1 according to the method of the invention, in which the sensitivity of absorbance in FIGS. 3 to 5 is about 1/10 of that in FIGS. 6 to 17.
Figure 4:
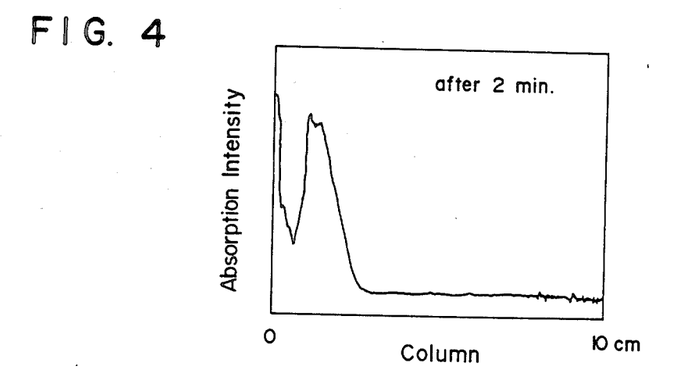
Figure 5:
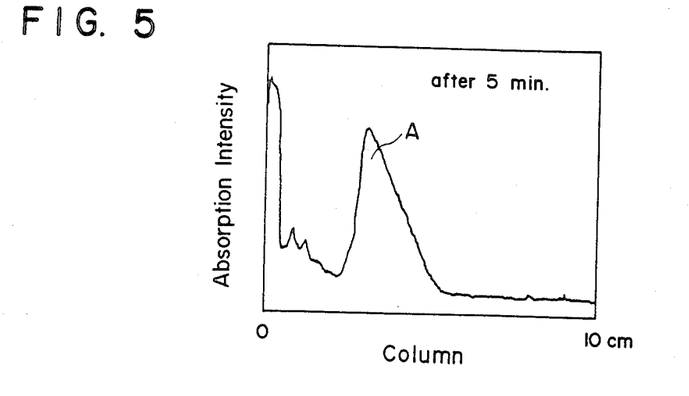
Figure 6:
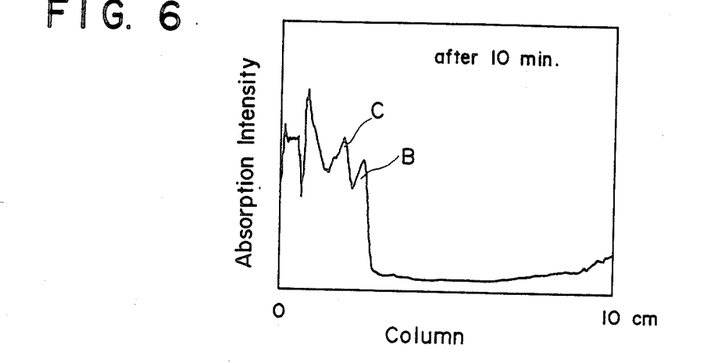
Figure 7:
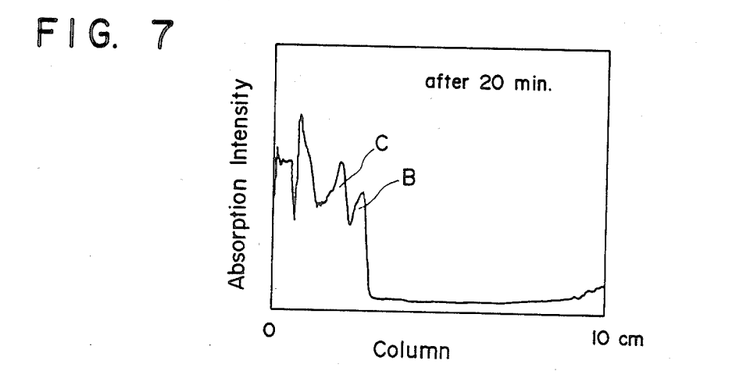
Figure 8:
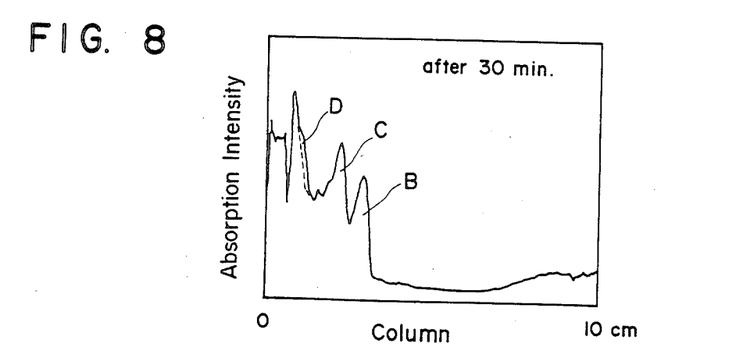
Figure 9:
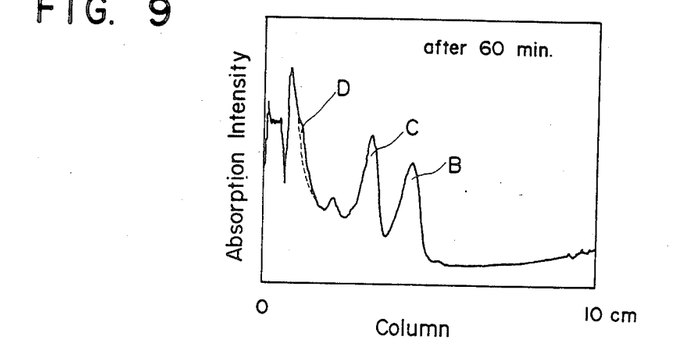
Figure 10:
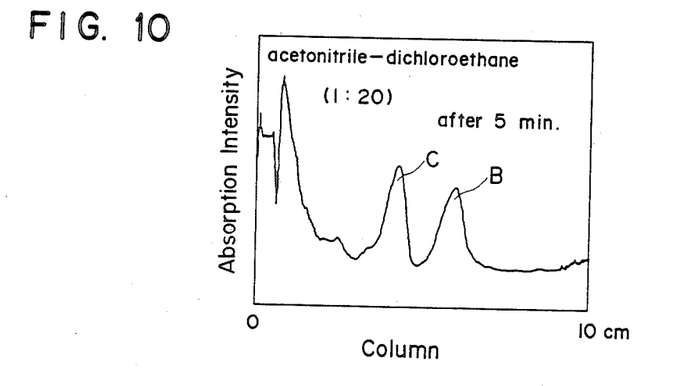
Figure 11:
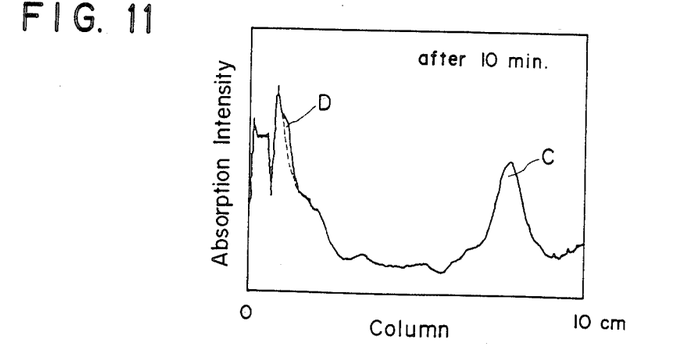
Figure 12:
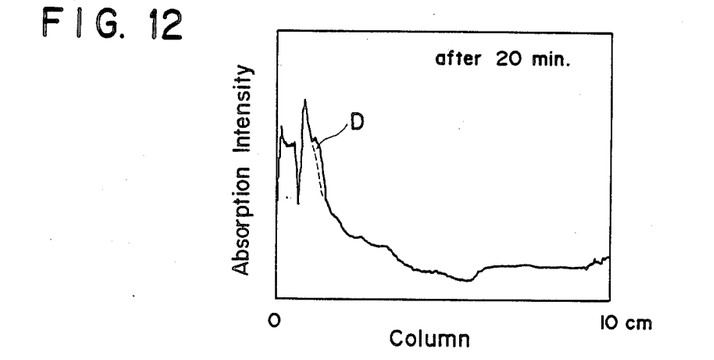
Figure 13:
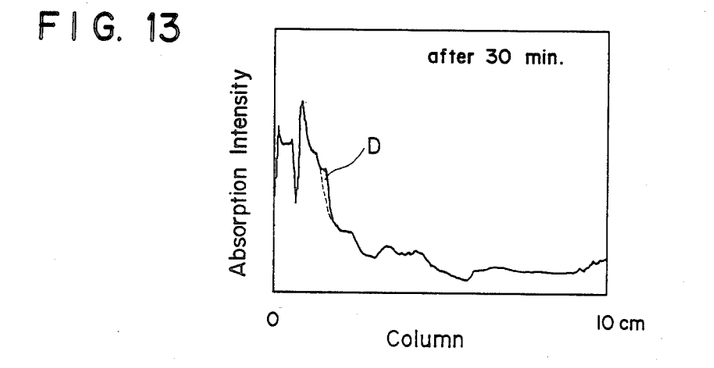
Figure 14:
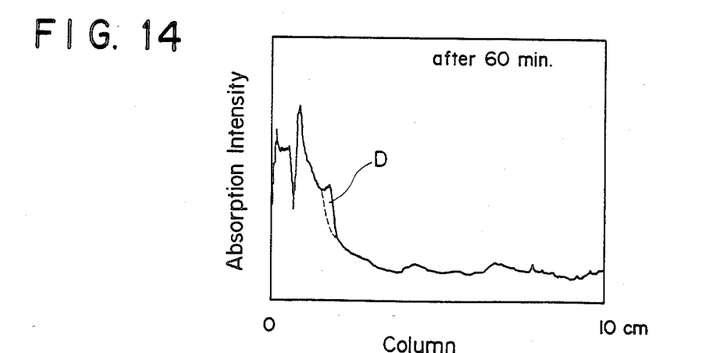
Figure 15:
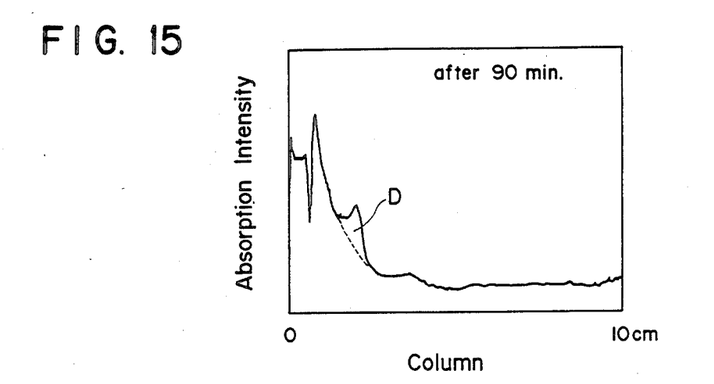
Figure 16:
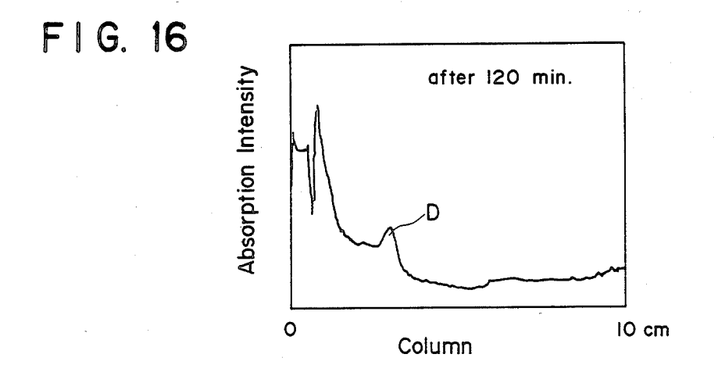
Figure 17:
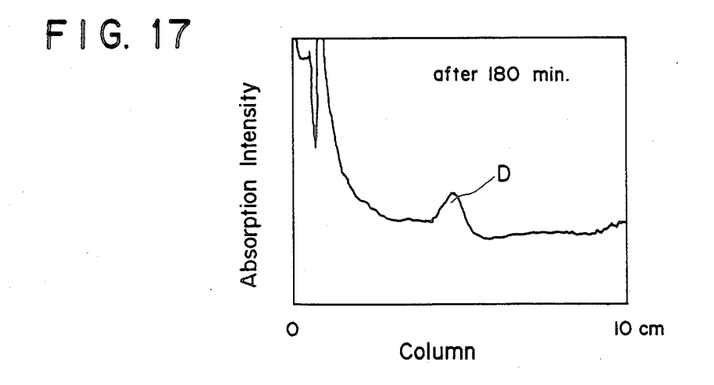

FIG. 2 illustrates an apparatus for steady or non-pulse irradiation mentioned above, which is the same apparatus as in FIG. 1 except the partition wall has been omitted and a fluorescent lamp 16 is used in place of the pulse lamp.

Other features of the invention will become apparent in the course of the following description of exemplary embodiments which are given for illustration of the invention and are not intended to be limiting thereof.

EXAMPLES

Reference Example 1.0 g of high grade disodium protoporphyrin was suspended in 50 ml of water, and added to 450 ml of separately prepared 40% hydrochloric acid, followed by stirring for 1 hour at 20° C. After the reaction was complete, the reaction liquid was instantly put into 3.9 l of 5% aqueous solution of NaOH, which was adjusted to pH 3 by adding 5% aqueous sodium acetate. The precipitates which occurred at this time were filtered out and, after washing with water, dried under reduced pressure. The reaction product thus obtained was dissolved in 100 ml of a solution of 3 ml of ether solution containing 47% BF$_3$ etherate and methanol. After reaction for 1 hour at 40° C., triethylamine was added for neutralization. The neutralized liquid was then extracted with dichloromethane. After washing with water three times, the dichloromethane layer was separated and dried with sodium sulfate. An equivalent amount of methanol was added and dichloromethane was gradually distilled off by the use of an evaporator. The distillation was stopped upon precipitation of crystals and the solution cooled. 0.4 g of protoporphyrin dimethylester were obtained by filtration of the precipitated crystals. The solvent in the filtrate was distilled off by the use of an evaporator, obtaining a mixture of protoporphyrin dimethylester (A), 3-hydroxyethyl-8-vinyldeuteroporphyrin dimethylester (B), 3-vinyl-8-hydroxy-ethyldeuteroporphyrin dimethylester (C), and hematoporphyrin dimethylester (D).

Example 1

The mixture obtained in Reference Example 1 was chromatographed using an apparatus as shown in FIG. 1, detecting the condition and pattern of separation in the following manner.

The chromatography was carried out using a Pyrex column (4 mm×200 mm) packed with silica gel SI-60 (a product of Merck & Co., Inc.), desorbing the components by eluting with dichloroethane at a rate of 1.0 ml/min for 60 minutes and thereafter eluting with acetonitrile-dichloroethane (1:20) at a rate of 1.0 ml/min by means of a pump (model 510 Waters, Inc.). A highly stable xenon pulse lamp (a product of Hamamatsu Photonics, Inc.) was used as a light source and the intensity of the transmitted light was measured by a line sensor (DLS-2048, a product of Dynamics, Inc.). The time period of the pulse irradiation was 0.5 second.

The signals which were obtained from the line sensor in this manner were sent to the computer through the A/D converter, processing the signals by the computer to make a separation pattern at one minute intervals after initiation of desorption as shown in FIGS. 3 to 17.

Figure 18:
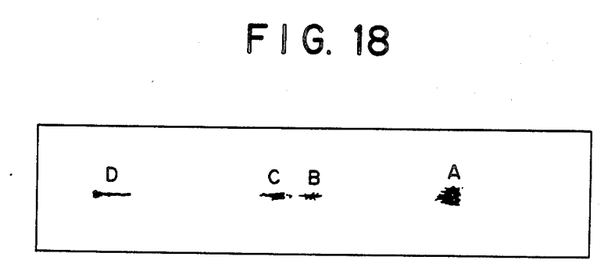
FIG. 18 is a diagrammatic illustration of a thin layer chromatogram obtained by TLC in Example 1.
Figure 19:
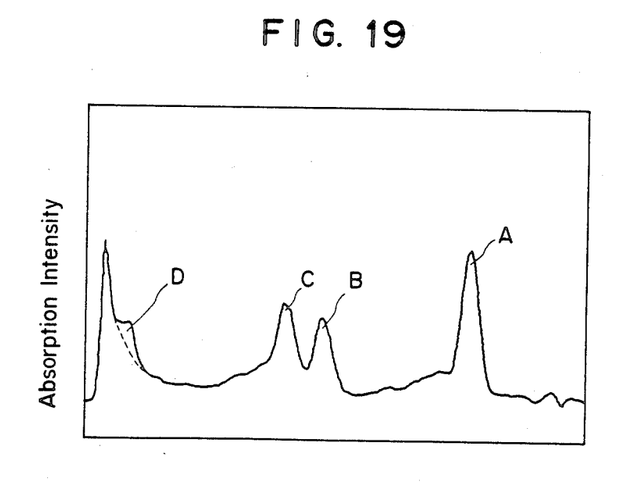
FIG. 19 is a diagram of a separation pattern detected from the thin layer chromatogram.

For the purpose of comparison with the method of the present invention, FIG. 18 shows a thin layer chromatogram which was obtained by separating the same sample material by TLC using a silica gel plate (a product of Merck & Co., Inc.) and dichloromethane as the developing solvent. Shown in FIG. 19 is the separation pattern which was obtained from the thin layer chromatogram using a line sensor in the same manner as in the present invention.

Figure 20:
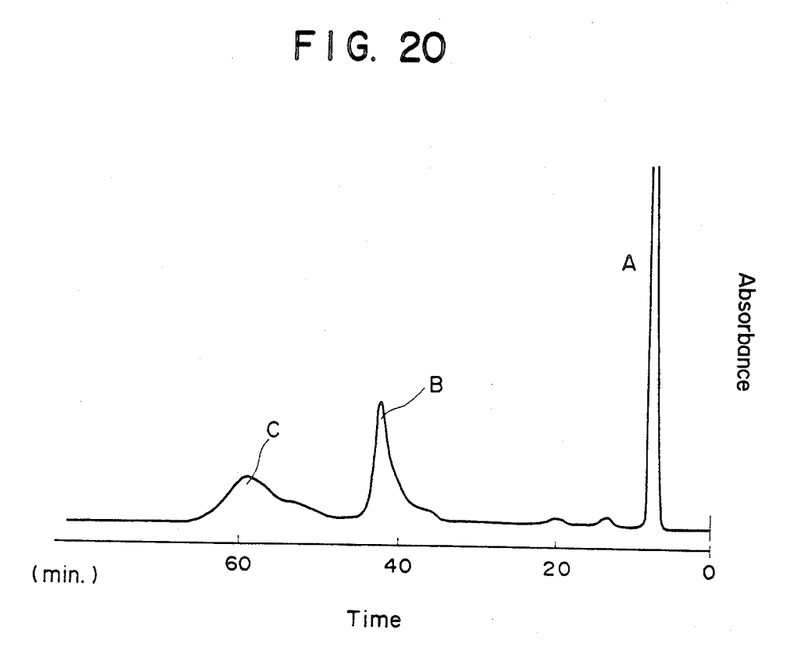
FIG. 20 is a diagram of a chromatogram obtained by the use of conventional HPLC in Example 1.

Further, FIG. 20 shows a chromatograpm which was obtained by separating the same sample material using conventional HPLC (detecting the solutes by a flow cell) using a column packed with silica gel SI-60 and acetonitrile-dichloroethane (1:20) as the developing solvent. Under these conditions, the existence of component D was not detected.

The high-performance liquid chromatography method of the present invention has the advantages of both conventional TLC and HPLC as mentioned above. It enhances the effectiveness of chromatography by improvements, for example, in the following aspects:

(i) As the method of the present invention employs the closed system of HPLC, it is free of the problem of diffusion of separated substances as in TLC and allows charging of a sample material accurately.

(ii) The method of the present invention detects the separating conditions and separation patterns in a column as a whole. In this way it can detect all of the components as in TLC, eliminating the inability of HPLC to detect the adsorbed residues in a column. It follows that the separation or adsorption of the respective components can be easily detected with confidence.

(iii) According to the method of the present invention, one can detect the variations in the separation pattern in a column from the separation pattern which is detected at arbitrarily predetermined time intervals. This dynamic and sequential information related to the separation pattern facilitates the setting of separating conditions which has thus far been a problem in the application of HPLC. That is to say, it facilitates the selection of the packing material, desorbing solvent and its flow rate, length of the column, etc.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A high performance liquid chromatograph comprising an apparatus for detecting separating conditions and separation patterns, comprising:
   a light-shielding chamber;
   a light source located within said chamber;
   a line sensor located in said chamber for detecting light and producing a sensed light signal;
   a transparent separation column extending parallel with said line sensor and positioned between said light source and said line sensor;
   means for pumping a sample through said column; and
   means for processing said sensed light signal from said line sensor.

2. The high performance liquid chromatograph of claim 1, wherein said light source is a pulsed xenon light source.

3. The high performance liquid chromatograph of claim 1, wherein said light source is a fluorescent lamp.

4. The high performance liquid chromatograph of claim 1, wherein said processing means comprises:
   an A/D converter, for receiving said signal from said line sensor; and
   a computer for processing and storing said signal from said A/D converter.

5. The high performance liquid chromatograph of claim 2, further comprising a partition wall in said chamber between said light source and said column, said partition wall having a horizontal slit substantially the same length as said column and parallel with said column whereby said line sensor senses light transmitted through said separation column.

6. The high performance liquid chromatograph of claim 1, wherein said light source is a fluorescent light.

7. The high performance liquid chromatograph of claim 1, wherein said transparent separation column is comprised of glass or quartz.

8. A method of detecting separating conditions and separation patterns in high performance liquid chromatography, comprising the steps of:
   charging a sample onto a glass or quartz high performance liquid chromatography column;
   eluting the sample through said column;
   irradiating substantially the entire length of said column with a light source; and
   detecting the intensity of reflected, transmitted or fluorescent light from said column with a line sensor.

9. The method of claim 8, wherein said irradiating step is performed with a pulsed xenon light source.

10. The method of claim 8, wherein said irradiating step is performed with a fluorescent light source.

* * * * *